United States Patent [19]

Anderson

[11] 4,451,781
[45] May 29, 1984

[54] MOISTURE TESTER
[75] Inventor: James W. Anderson, Tulelake, Calif.
[73] Assignee: Sarah Anderson, Tulelake, Calif. ; a part interest
[21] Appl. No.: 265,279
[22] Filed: May 20, 1981
[51] Int. Cl.³ ............................................. G01R 27/02
[52] U.S. Cl. .................................. 324/65 R; 324/65 P
[58] Field of Search .................... 324/65 R, 65 P, 61 P
[56] References Cited

U.S. PATENT DOCUMENTS

| | | | |
|---|---|---|---|
| 1,910,021 | 5/1933 | Legg | 324/65 P |
| 2,579,316 | 12/1951 | Hall et al. | 324/65 R |
| 2,621,232 | 12/1952 | Spalding | 324/65 R |
| 2,754,478 | 7/1956 | Goldsmith | 324/61 P |
| 2,906,952 | 9/1959 | Horecky | 324/65 P |
| 2,975,361 | 3/1961 | Holaday | 324/65 R |
| 3,141,129 | 7/1964 | Dietert | 324/65 R |
| 3,229,200 | 1/1966 | Rayburn | 324/65 R X |
| 3,689,832 | 9/1972 | Leto et al. | 324/65 R |
| 3,758,855 | 9/1973 | Meyer | 324/65 R |
| 3,901,214 | 8/1975 | Taaffe | 324/65 R UX |
| 3,936,735 | 2/1976 | de Bough | 324/65 R X |
| 3,944,916 | 3/1976 | Tillander | 324/65 P |
| 4,004,223 | 1/1977 | Cohen | 324/65 P X |
| 4,123,701 | 10/1978 | Josefsen et al. | 324/65 R X |

Primary Examiner—Stanley T. Krawczewicz
Attorney, Agent, or Firm—Townsend and Townsend

[57] ABSTRACT

A moisture tester for measuring the total moisture content of high moisture feed products such as corn, silage and cut hay including a probe or sensor having spaced apart electrodes in contact with the product. A VCO is coupled to the electrodes for producing a variable frequency signal proportional to the resistance across the electrodes. A time base signal generator produces a relatively slow fixed frequency time base signal. A gate timer produces latch and reset signals from the time base signal for use in a BCD counter incorporating latch, multiplex and BCD counter portions. The resulting output from the BCD counter drives a display device to provide the user with a relative indication of the amount of moisture over a range of moistures in the feed product. Also disclosed are several types of probes. One flat plate type includes coaxially-mounted annular electrodes for measuring the moisture of newly cut hay. Another sensor measures the moisture of loose feed products using a conical bucket having electrodes mounted on its interior walls.

5 Claims, 8 Drawing Figures

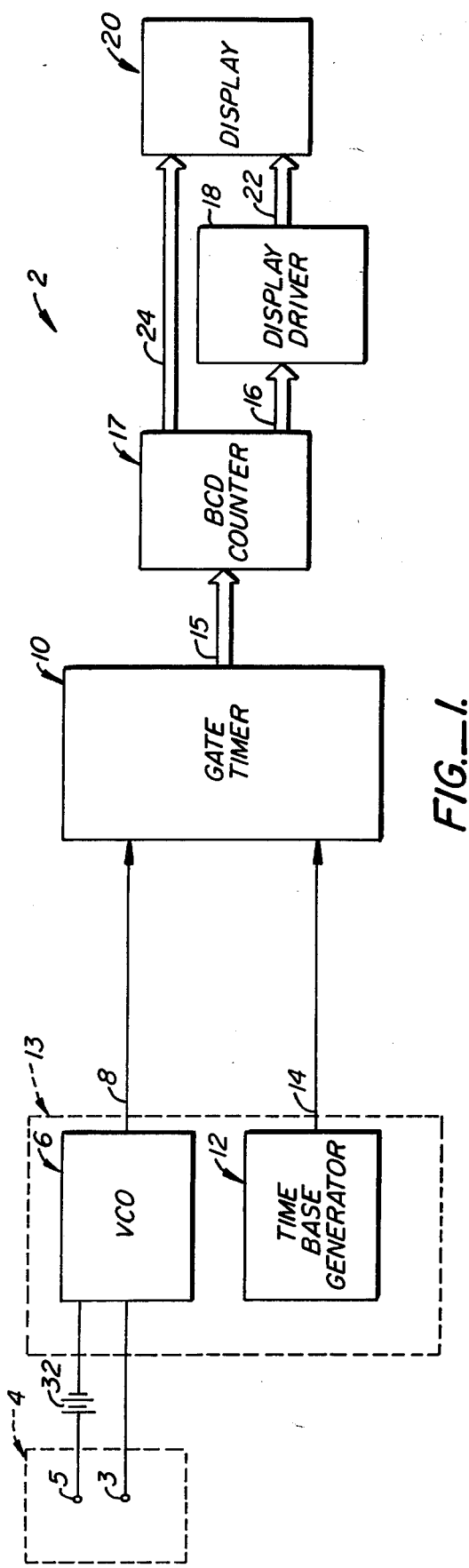
FIG._1.
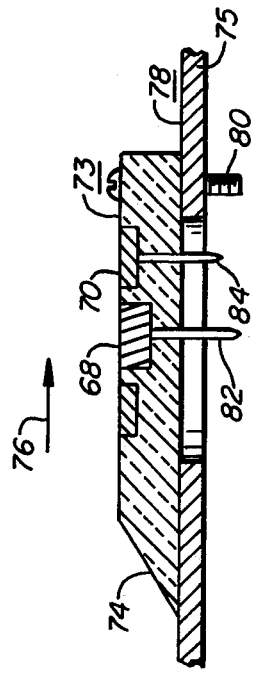
FIG._3B.
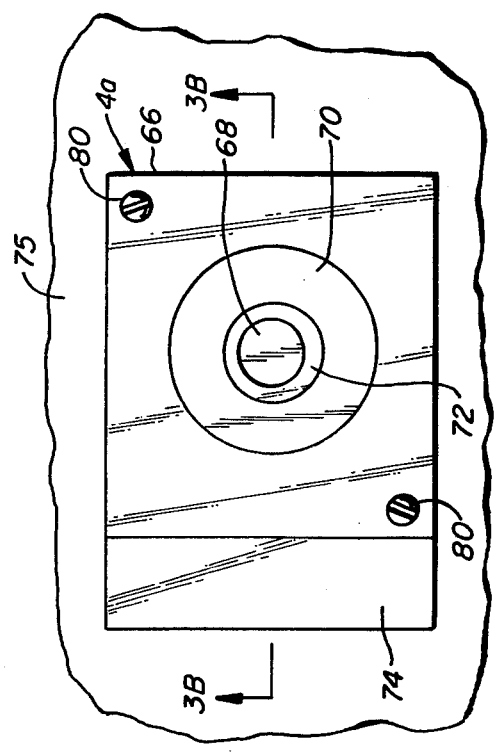
FIG._3A.

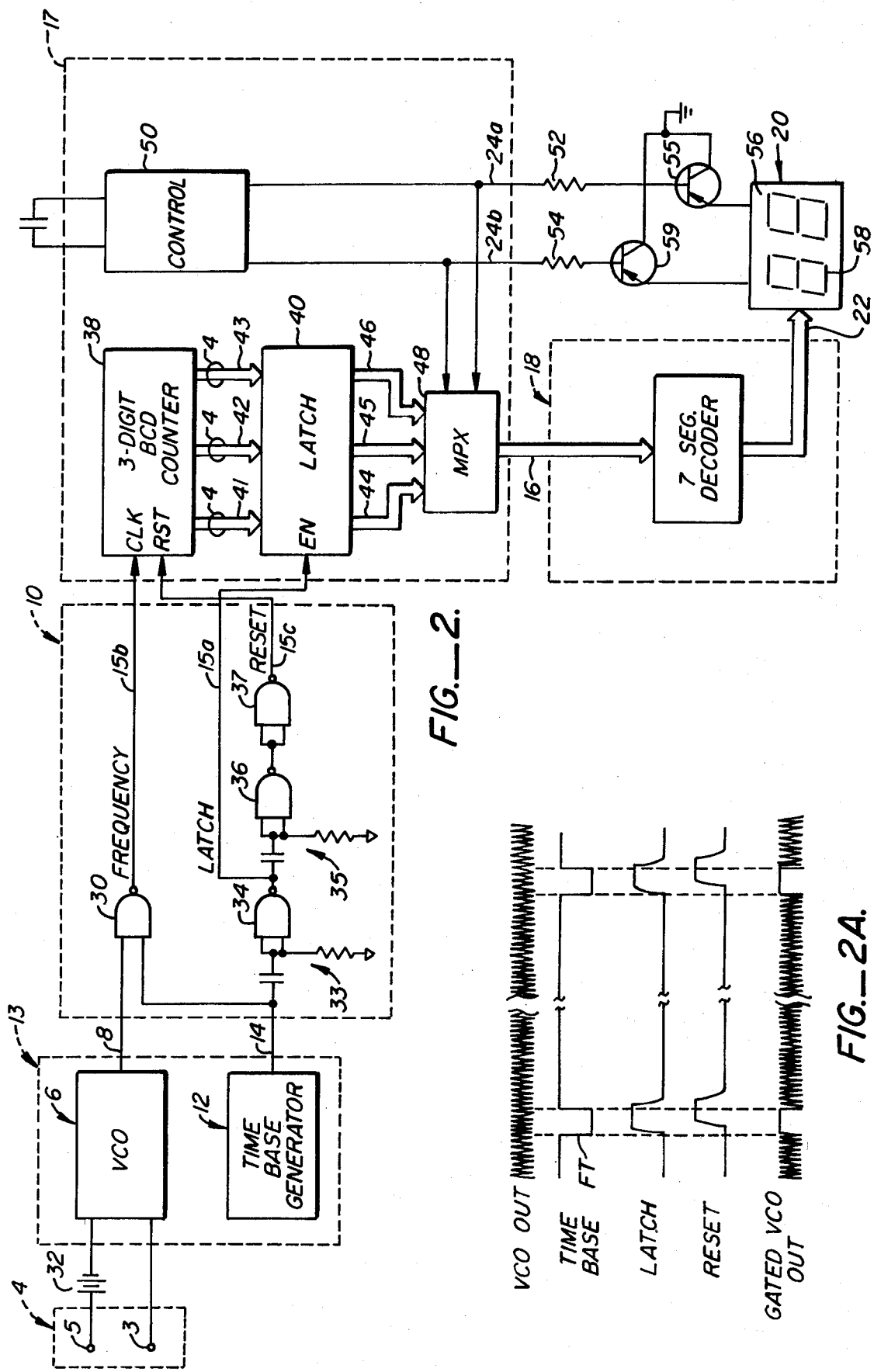

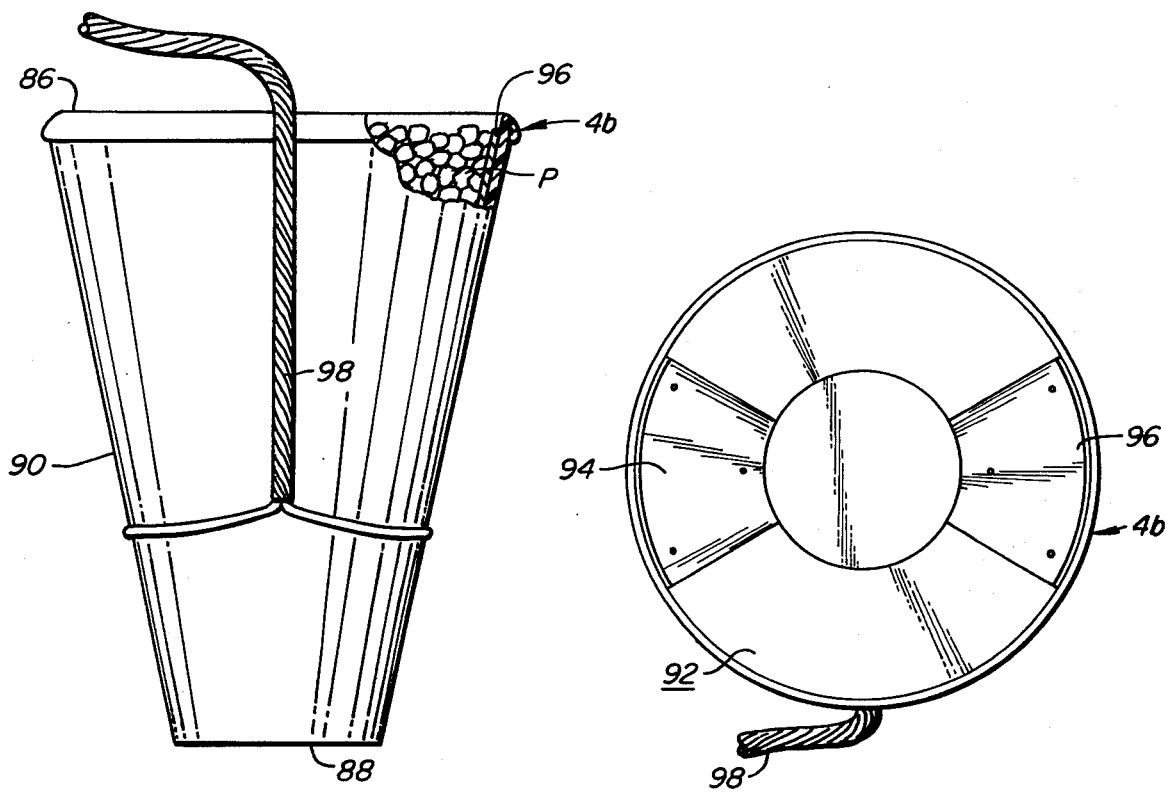
FIG._4A.　　　　　FIG._4B.
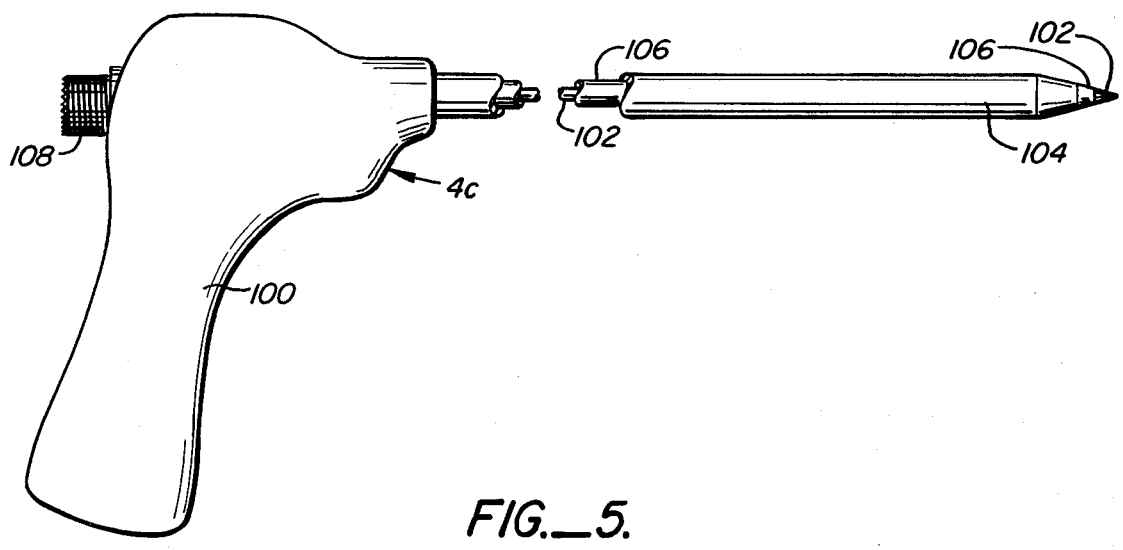
FIG._5.

MOISTURE TESTER

BACKGROUND OF THE INVENTION

Accurate measurement of the moisture content in feed products such as hay and silage is important for several reasons. For example, it is the moisture content in silage that causes chemical changes in the silage, resulting in the breakdown of some cellulose and the increase in the digestable sugars. Therefore, silage having the proper moisture content and stored properly has its food value improved. However, if the moisture content of the silage is too high, the silage will tend to ferment in an uncontrolled fashion. Alternately, if the moisture content is too low, the silage can mold and spoil.

Many farm crops when picked at the height of maturity can be stored only after being partially dried. Hay commonly contains 70-80% moisture when harvested and must be dried to about 20% moisture when stored in bales and to about 22-25% moisture when stored as chopped hay. Insufficiently dried hay can mold and can be ruined as a feed product. Overdried hay can lose much of its nutritional value.

Moisture testers have been developed for measuring the moisture content of grain. In U.S. Pat. No. 4,044,607 a moisture measurement probe is disclosed for measuring the moisture content of grain. This probe uses the dielectric constant of the grain to analyze its moisture content and is insulated from and unaffected by electrical resistance of the grain. It is therefore not particularly suited for measuring the total moisture content of products to include internal and external moisture of the product. Other moisture testers which may be of interest are disclosed in U.S. Pat. Nos. 3,175,391 and 2,105,683.

SUMMARY OF THE INVENTION

A moisture tester is disclosed which is particulary suited for measuring the moisture content of hay moisture feed products such as corn, silage and cut hay. The tester uses a sensor or probe having spaced apart electrodes in contact with the product for measuring the electrical resistance of the product. The probe is connected to a voltage controlled oscillator (VCO) and provides the VCO an electrical signal that is proportional to the resistance across the electrodes. The VCO converts the signal from the probe into a variable frequency signal, the frequency of which is proportional to the resistance across the electrodes. A relatively slow, fixed-frequency time base signal is provided by a time base signal generator.

A gate timer receives the variable frequency signal from the VCO, gates it to a BCD counter. The gate timer uses the time base signal to produce latch and reset signals to control the operation of the BCD counter. The BCD counter, incorporating a BCD counter portion, a latch and a multiplexer, takes the gated variable frequency signal, the latch signal and the reset signal to produce a BCD output signal in the form of a multiple bit data word that is representative of the resistance across the electrodes of the probe and, therefore, indicative of the moisture content of the measured quantity. The BCD signal is routed through a display driver to a digital display device to provide the user with a relative indication of the total amount of moisture in and on the product.

Several configurations for the probes are also disclosed. One flat plate type includes coaxially-mounted annular electrodes. This type is typically mounted on the sidewall of a hay baler and is positioned so that the electrodes contact the newly severed ends of the baled hay. By such configuration and positioning, the total moisture content, that is the external moisture on the outside of the hay as well as the cellular moisture within the hay, can be measured. A second type of probe uses a conical bucket or cup having opposed, spaced-apart electrodes mounted on the interior walls of the bucket. This sensor is used to measure the moisture of loose, high moisture products. The inwardly and downwardly tapered side insures that a reliable moisture readings can be obtained. A hand held probe for manual insertion into a product is also disclosed.

A primary feature of invention is its use of a VCO to convert the analog resistance measurement to a variable frequency signal and a relatively slow frequency time base signal. The two signals are used to drive a gate timer and a BCD counter circuit to produce a digital output on a numerical display. The entire circuit can be made of standard components to keep the cost low. Its digitized output is also compatable with microprocessor circuitry for automatic control of the moisture in a product line.

The invention does not attempt to read moisture on a direct percentage of moisture basis. Rather, it gives a relative reading of moisture over a range of moistures. For example, when set for one moisture range a reading of 00 on the two digit digital display may represent 12% moisture while a reading of 99 may represent 35% moisture. By not attempting to achieve a precise moisture percentage reading but rather a representative moisture reading corresponding to a certain percentage of moisture, the device is less complex.

Another significant aspect of the invention is the provision of a probe or sensor having coaxial, annular flat plate electrodes for the measurement of the moisture content of freshly cut hay. This probe, typically mounted to a side wall of a baler so that the electrodes contact the ends of the freshly cut hay, provides an accurate total moisture content reading of the hay. It has been found that due to the resistance of the hay, measurement of the moisture content by resistance techniques without exposing the electrodes to the cut ends of the hay measures primarily only the surface moisture of the hay, thereby reducing the accuracy. Also, by configuring the electrodes concentrically, current grounding, which can cause erroneous readings, is effectively eliminated. Both of these problems, that is measurement of the total moisture content of hay and the elimination of current grounding, are effectively elminated by the coaxial, annular flat plate probe of the present invention.

Measurement of the moisture content of high moisture content bulk items, such as corn and moist grain, is facilitated by the use of the conical bucket sensor. The inwardly and downwardly sloping sides insure that an appropriate pressure is exerted against the electrodes so the moisture measurement is accurate quite reproducable. A similar bucket, but lacking the tapered sides, has been found not to yield such reproducible readings.

Other features and advantages of the present invention will be apparent from the following description in which the preferred embodiment has been set forth in detail in conjunction with the accompanying drawings.

BRIEF DESCRIPTION OF THE DRAWINGS

FIG. 1 is a block diagram of a moisture tester made according to the present invention.

FIG. 2 is a more detailed diagram of the tester of FIG. 1.

FIG. 2A is a timing diagram illustrating several of the signals.

FIGS. 3A and 3B are top and side views of a probe having coplanar annular electrodes.

FIG. 4A is a side view of a conical probe, shown filled with a product, made according to the present invention.

FIG. 4B is a top view of the probe of FIG. 4A without the product.

FIG. 5 is a side view of a hand held probe.

DETAILED DESCRIPTION OF THE PREFERRED EMBODIMENT

Turning now to FIG. 1, tester 2 is shown as broadly including a probe 4 having an anode 3 and a cathode 5 coupled to a voltage controlled oscillator (VCO) 6 which produces a variable frequency signal that is coupled by a signal line 8 to a gate timer 10. A time base generator 12 produces a time base signal having a fixed frequency that is coupled along a signal line 14 for input into gate timer 10. Gate timer 10 operates to produce from the received signals gate timing signals, including a gated portion of the variable frequency signal from the VCO 6, on multiple signal lines 15 which are connected to a BCD counter 17. Counter 17 operates to produce signals in the form of a multiple-bit data word count. Multiple signal lines 16 couple this data word to a display driver 18. A display 20, having two numeric characters, is provided character segment signals by driver 18 via multiple signal lines 22. Multiple lines 24 connects BCD counter 17 with display 20 and provides display 20 which character enable signals.

Turning now also to FIG. 2 the circuit will be described in more detail. VCO 6 and time base generator 12, which may be two separate elements, are preferably combined as a single circuit component 13. Such circuit components are commercially available from a number of circuit manufacturers such as, for example, Intersil, Inc of Cupertino, Calif., which sells such a circuit component under the part number 556. Anode 3 is connected to the positive terminal of a nine volt battery 32 while the negative terminal of battery 32 is connected to circuit component 13.

VCO 6 produces a square wave output on line 8, the frequency of which varies in proportion to the resistance across anode 3 and cathode 5 of probe 4. This signal is represented in FIG. 2A as VCO Out. A TIME BASE signal on line 14, shown in FIG. 2A as TIME BASE, is provided gate timer 10 which may be a commercially available component (a Quad NAND Gate) such as that sold by Intersil, Inc. as part number MC 14011. As can be seen from FIG. 2A, the frequency of the time base signal is relatively long so that an appropriate number of signal pulses from VCO 6 can be counted over one cycle of the time base signal.

The signals on lines 8 and 14 are each coupled to one of two inputs of a two-input NAND gate 30 which produces a gated frequency output signal on line 15b to BCD counter 17. This signal is shown in FIG. 2A as GATED VCO OUT. The TIME BASE signal on line 14 is also coupled to an inverter 34 through an RC network 33. The output of inverter 34 is used at a latch signal on line 15a for input into counter 17. RC network 33 causes a slight delay in the LATCH signal relative to the time base signal, as shown in FIG. 2A. The output from inverter 34 is applied to a second RC network 35 and coupled, by a pair of two-input NAND gates 36, 37 to signal line 15c as a RESET signal. The RESET signal, as seen in FIG. 2A is delayed somewhat from the LATCH signal on line 15a by the second RC network 35.

BCD counter 17, which may be a standard component such as that made by Intersil, Inc. and sold under part number MC 14553, includes a three digit (each digit comprising four binary stages) BCD counter portion 38 to which lines 15b and 15c are connected. Counter portion 38 feeds a latch 40 via multiple lines 41, 42 and 43. Since display 20 is only a two digit display, the count on only two of the three multiple lines are important. Signal line 15a couples the LATCH signal to the enable (EN) input of latch 40, causing the latch to accept and store the count then obtained (i.e., when the LATCH signal is present) by the counter portion 38, the latched count then appears on the output lines 44, 45, and 46.

Display driver 18 can be a standard component such as that made by Intersil, Inc. as part number MC 14511.

Character segment signals are provided display 20 via multiple lines 22. Signal lines 24a and 24b are coupled by resistors 52, 54 to transistor switches 55 and 59 to form character enable signals having a split duty time so that during one portion of the duty time a first LED numeral 56 is activated by character segment signals on multiple signal lines 22. Similarly a second LED numeral 58 is enabled by an enable signal from the transistor switch 59.

Prior to describing the various configurations for the probe, the operation of the tester will be described briefly. Anode 3 and cathode 5 of probe 4 are placed in contact with a product for which the relative moisture content is to be determined.

Component 13 produces the VCO OUT signal on line 8, corresponding to the resistance between anode 3 and cathode 5, and the time base signal on line 14. Enabling the NAND gate 34 with the time base signal, allowing predetermined portions of the VCO out signal to pass to and be counted by the counter portion 38, allows the count obtained (by the counter portion 38) to represent a moisture content of the measured quantity. The slight delay in the LATCH signal (relative to the fall time TF of the time base signal) ensures that the counter portion 38 finishes counting the count before obtained is transferred to latch 40. Similarly, delaying the RESET signal from the LATCH signal ensures that counter portion 38 is not reset before latch portion 40 obtains the count.

MPX 48, under control of the control signals provided on lines 24a and 24b by control portion 50, provides the multiple bit data word along multiple lines 16 to the display driver 18 in multiplexed fashion; that is, the four-bit BCD count used to illuminate the LED numeral 58 is communicated to the display driver 18 (a seven segment decoder) during a first time period; then, the four-bit BCD count used to illuminate the LED numeral 56 is communicated to the display driver during a second time period. Thus, MPX 48 sequentially alternates between communication of the two low-order, four-bit BCD stages of the latch 48 to the display driver 18. The display drive provides display 20 with appropriate character segment signals on multiple signal lines 22 to illuminate either numeral 56 or numeral 58 according to presence of character enable signal on lines 24a or 24b respectively. The duty cycle frequency is sufficiently rapid so that flickering of the LED numerals is not noticeable. Through the use of multiplex portion 48 and control portion 50, the two digit display 20 can be driven by a single display driver 18.

Turning now to FIGS. 3-5, various configurations of probes 4 will be described. In FIGS. 3A and 3B probe 4a is shown having a generally rectangular body 66 made of an electrical insulator. A pair of concentric electrodes including a central disk-like anode 68 and an annular cathode 70 circumscribing anode 68 and spaced apart by a gap 72 is mounted to an outer surface 73 of body 66. Body 66 includes a leading beveled edge 74. Probe 4a is typically mounted to a sidewall 75 in the bale chamber on a baler or on any other surface against which a moisture containing product may pass. Beveled edge 74 allows the product passing in the direction of arrow 76 to proceed relatively smoothly past probe 4a. The probe can also be mounted so that its outer surface 73 is flush with the interior surface 78 of sidewall 75. A pair of mounting bolts 80 are provided for mounting probe 4a to sidewall 75 of the baler. A pair of leads 82, 84 extend from anode 68 and cathode 70 respectively for electrical connection with the circuit.

The concentric, typically flat configuration of probe 4a allows the automatic sensing of the relative moisture content of a high moisture content product, such as freshly cut hay, while moving the bale chamber of a baler. It could also be used in many other structures against or along which an appropriate product passes.

In FIGS. 4A and 4B a conical, cup-like probe 4b is shown having a generally open top 86, a closed bottom 88 and a circumferential sidewall 90 tapering inwardly from top 86 to bottom 88. A pair of spaced-apart electrodes 94, 96 are mounted against along the inside surface 92 of sidewall 90. These electrodes are electrically coupled to the circuit as shown in FIGS. 1 and 2 via cable 98. The use of probe 4B is simple; it is merely filled to a constant height, typically to top 86, with a product P having a relatively high moisture content, such as corn or silage. The downwardly and inwardly sloping electrodes 94, 96 provide for effective electrical contact between electrodes and the product for reliable measurement of the degree of moisture in a product.

At FIG. 5 a hand held probe 4c is shown having a molded handle 100 from which an anode 102 and cathode 104 separated by an insulator 106 extends. The electrodes are connected to the circuit of FIG. 2 through a conventional connecter 108. The user merely forces the pointed coaxial anode 102 and cathode 104 into the product, such as high moisture corn and grain, to take a moisture reading of the product.

Modification and variation may be made to the disclosed embodiment without departing from the subject of the invention as defined in the following claims.

I claim:

1. An instrument for producing a digitized signal respresentative of the moisture content of a product over a range of moisture contents, comprising:
    a probe having spaced-apart electrodes for contact with said product;
    converter means, electrically coupled to said electrodes of said probe, for producing a first signal at a first output having a first frequency generally proportional to the resistance across said electrodes;
    clock means for producing a standard frequency signal at a second output;
    a gate timer circuit electrically connected to said first and second outputs; and
    digital counter circuit means, electrically coupled to said gate timer circuit, for producing a digitized output signal at a third output, said digitized output signal being a digital representation of a value proportional to the resistance across said electrodes.

2. The instrument of claim 1 further comprising:
    a display driver electrically coupled to said third output at a driver input and having a driver output; and
    digital display device having a display input electrically coupled to said driver output at the display input whereby an indication of the moisture of said product as sensed by said electrodes is displayed.

3. The instrument of claim 1 wherein:
    said probe is a planar structure in which said electrodes are on an outer surface thereof;
    said electrodes include a first electrode having a first electrode surface and a second electrode having a second electrode surface surrounding the first electrode surface, said electrode surfaces lying in an electrode plane; and
    wherein said probe is arranged and adapted to be mounted to the sidewall of a hay baler with said electrode surfaces exposed to hay so that the instrument measures the relative moisture content of a hay crop as the electrode surfaces make contact with the cut ends of the hay within the baler.

4. The instrument of claim 1 further comprising an electric current source coupled to one of said electrodes.

5. The instrument of claim 1 wherein said probe comprises a container having an inwardly and downwardly sloping circumferential sidewall having an interior surface and an exterior surface and wherein said electrodes are mounted on the interior surface of said sidewall for contact with the product within said container whereby the sloping walls insure that reproducible moisture measurements are obtained.

* * * * *